United States Patent
Kato et al.

(10) Patent No.: US 6,881,866 B2
(45) Date of Patent: Apr. 19, 2005

(54) PROCESS FOR PRODUCTION OF POLYALKYL-SUBSTITUTED AROMATIC ALDEHYDE

(75) Inventors: Kinji Kato, Okayama (JP); Tsuyoshi Hatakeyama, Okayama (JP); Mitsuharu Kitamura, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 10/615,297

(22) Filed: Jul. 9, 2003

(65) Prior Publication Data

US 2004/0092776 A1 May 13, 2004

(30) Foreign Application Priority Data

Nov. 7, 2002 (JP) ........................................ 2002-203020

(51) Int. Cl.[7] .............................................. C07C 45/49
(52) U.S. Cl. ........................................ 568/428; 568/437
(58) Field of Search ................................ 568/428, 437

(56) References Cited

U.S. PATENT DOCUMENTS 2,485,237 A * 10/1949 Gresham et al. ............ 568/428
3,948,998 A * 4/1976 Fujiyama et al. ............ 260/599
4,460,794 A * 7/1984 Fujiyama et al. ............ 568/428

FOREIGN PATENT DOCUMENTS

EP  0 083 224    7/1983
GB  1 422 308    1/1976

OTHER PUBLICATIONS

European Search Report mailed Oct. 2, 2003, for EP 03 01 4141.

* cited by examiner

Primary Examiner—Johann Richter
Assistant Examiner—Sikarl A. Witherspoon
(74) Attorney, Agent, or Firm—Antonelli, Terry, Stout & Kraus, LLP

(57) ABSTRACT

In the process of the present invention, a polyalkyl-substituted aromatic aldehyde is produced by the formylation of a corresponding polyalkyl-substituted aromatic compound with carbon monoxide in the presence of hydrogen fluoride/boron trifluoride catalyst. By limiting the amount of hydrogen fluoride to a specific range, the formylation rapidly proceeds under mild conditions without causing the precipitation of solid matters even when the starting polyalkyl-substituted aromatic compound has alkyl groups on both the carbon atoms adjacent to the site to be formylated.

9 Claims, No Drawings

PROCESS FOR PRODUCTION OF POLYALKYL-SUBSTITUTED AROMATIC ALDEHYDE

BACKGROUND OF THE INVENTION

1. Field of the Invention

The present invention relates to a process for producing polyalkyl-substituted aromatic aldehydes having three or more $C_1$–$C_3$ alkyl groups which are useful as a raw material or an intermediate material for the production of medicines, agricultural chemicals, perfumes, etc.

2. Description of the Prior Art

Gattermann-Koch reaction has been well known in the art as a production method of an alkyl-substituted aromatic aldehyde by formylating an alkyl-substituted aromatic compound with carbon monoxide in the presence of a catalyst such as a hydrogen chloride-aluminum chloride catalyst. In this reaction, the reaction product mixture is generally treated with water to separate the reaction product and the catalyst, this making the regeneration of the catalyst extremely difficult. Further, a large amount of wastes are produced by hydrolysis to unfavorably increase disposal costs.

Modified Gattermann-Koch reactions using hydrogen fluoride and boron trifluoride as the catalyst are disclosed in U.S. Pat. No. 2,485,237, Japanese Patent Publication No. 39-29760, Japanese Patent Application Laid-Open No. 56-99433, etc. Since hydrogen fluoride and boron trifluoride used as the catalyst in the proposed modifications show a high vapor pressure, the hydrolysis is not needed to separate the reaction product and the catalyst, this allowing the catalyst to be recycled and reused. Therefore, the proposed modifications provide an industrially excellent process for the production of aromatic aldehydes.

In the formylation of the alkyl-substituted aromatic compounds in the presence of the hydrogen fluoride/boron trifluoride catalyst, the formylation mainly occurs at the para-position with respect to the alkyl substituent to give p-alkyl aromatic aldehydes. However, if the alkyl-substituted aromatic compound has, as in the case of mesitylene or isodurene, alkyl groups on both the carbon atoms adjacent to the site to be formylated, the formylation reaction thereof is extremely slow as compared with the formylation of other alkyl-substituted aromatic compounds. For example, "Journal of Japan Petroleum Society", Vol. 20, pp. 655 to 661 (1977) teaches that toluene is formylated under mild conditions and in a short reaction time (under carbon monoxide pressure of 30 atm (2.9 MPa) for 20 min) with a yield as high as 94%, whereas the formylation of 1,3,5-trimethyl benzene (mesitylene) provides only 79% yield even under severe conditions of a carbon monoxide pressure of 200 atm (19.6 MPa) and a long reaction time of 1.5 h.

U.S. Pat. No. 2,485,237 discloses that the conversion of mesitylene is 82.3% in the formylation of 0.3 mol of mesitylene in the presence of 1.0 mol of hydrogen fluoride and 1.0 mol of boron trifluoride under a pressure of 100 to 730 atm (9.8 to 71.5 MPa) for 11 min. The pressure range proposed therein is too broad, but the formylation of mesitylene appears to require a considerably high pressure.

Thus, the formylation of the alkyl-substituted aromatic compound having alkyl groups on both the carbon atoms adjacent to the site to be formylated requires an extremely high carbon monoxide pressure of 10 MPa or higher and/or a very long reaction time to make the process industrially disadvantageous. In particular, the use of a pressure as high as 10 MPa or more in extremely strong corrosive conditions due to the hydrogen fluoride/boron trifluoride catalyst is industrially less practicable.

SUMMARY OF THE INVENTION

An object of the present invention is to provide an industrially useful process for producing a polyalkyl-substituted aromatic aldehyde by rapidly formylating a corresponding polyalkyl-substituted aromatic compound under mild conditions.

As a result of extensive study for achieving the above object, the present inventors have found that, by limiting the amount of hydrogen fluoride to 2.5 to 5.0 mol based on one mole of a starting polyalkyl-substituted aromatic compound, the formylation of the polyalkyl-substituted aromatic compound, even if it has alkyl groups on both the carbon atoms adjacent to the site to be formylated, proceeds under mild conditions with a sufficient formylation rate without causing precipitation of solid matters to give the corresponding polyalkyl-substituted aromatic aldehyde in an industrially advantageous manner. The present invention has been accomplished on the basis of this finding.

Thus, the present invention provides a process for producing a polyalkyl-substituted aromatic aldehyde by formylating a polyalkyl-substituted aromatic compound in the presence of a hydrogen fluoride/boron trifluoride catalyst, wherein the amount of hydrogen fluoride is 2.5 to 5.0 mol and the amount of boron trifluoride is 1.0 to 2.5 mol per one mole of the polyalkyl-substituted aromatic compound.

DETAILED DESCRIPTION OF THE INVENTION

The starting polyalkyl-substituted aromatic compound may include aromatic compounds having three to five $C_1$–$C_3$ alkyl groups on their aromatic ring, preferably 1,3,5-trialkyl-substituted aromatic compounds, 1,2,3,5-tetraalkyl-substituted aromatic compounds, 1,2,4,5-tetraalkyl-substituted aromatic compounds and 1,2,3,4,5-pentaalkyl-substituted aromatic compounds. Examples thereof include polymethylbenzenes such as mesitylene, isodurene, durene and pentamethylbenzene; polyalkyl-substituted aromatic compounds having both methyl group and alkyl group other than methyl group such as 1-ethyl-3,5-dimethylbenzene, 1,3-diethyl-5-methylbenzene and 1-isopropyl-3,5-dimethylbenzene; and polyalkyl-substituted aromatic compounds having only alkyl groups other than methyl group such as 1,3,5-triisopropylbenzene and 1,2,3,5-tetraethylbenzene.

In the present invention, it is particularly important to limit the amount of hydrogen fluoride acting as both a catalyst and a solvent to a particular range, i.e., 2.5 to 5.0 mol, preferably 3.0 to 4.5 mol based on one mole of the starting polyalkyl-substituted aromatic compound. If less than 2.5 mol, the polyalkyl-substituted aromatic aldehyde produced by the formylation forms a complex with HF and $BF_3$ to precipitate from the hydrogen fluoride solvent, requiring complicated treatments.

The use of hydrogen fluoride more than 5.0 mol per one mole of the starting polyalkyl-substituted aromatic compound is industrially and economically disadvantageous because the formylation becomes excessively slow and the amount of hydrogen fluoride to be recovered increases.

In contrast, the formylation proceeds more rapidly with increasing amount of hydrogen fluoride in the case of alkyl-substituted aromatic compounds, such as toluene, other than 1,3,5-trialkyl-substituted aromatic compounds, 1,2,3,5-tetraalkyl-substituted aromatic compounds, 1,2,4,5-tetraalkyl-substituted aromatic compounds and 1,2,3,4,5-pentaalkyl-substituted aromatic compounds.

Thus, the amount of hydrogen fluoride affects the rate of formylation of 1,3,5-trialkyl-substituted aromatic compounds, 1,2,3,5-tetraalkyl-substituted aromatic compounds, 1,2,4,5-tetraalkyl-substituted aromatic compounds and 1,2,3,4,5-pentaalkyl-substituted aromatic compounds in a different mode from the formylation of the other alkyl-substituted aromatic compounds. The reasons therefor are considered as follows.

The site to be formylated in 1,3,5-trialkyl-substituted aromatic compounds, 1,2,3,5-tetraalkyl-substituted aromatic compounds, 1,2,4,5-tetraalkyl-substituted aromatic compounds and 1,2,3,4,5-pentaalkyl-substituted aromatic compounds is subjected to a large steric hindrance by the alkyl groups on both the adjacent carbon atoms.

Hydrogen fluoride and boron trifluoride used as the catalyst are considered to form a 1:1:1 (by mol) complex with the starting polyalkyl-substituted aromatic compound. Hydrogen fluoride in excess of the starting polyalkyl-substituted aromatic compound participates in the formation of the 1:1:1 (by mol) complex by solvating the complex, thereby enhancing the steric hindrance of the alkyl groups on both the carbon atoms adjacent to the site to be formylated to reduce the rate of formylation.

Therefore, the steric hindrance on the site to be formylated is expected to be relieved by reducing the amount of excess hydrogen fluoride, thereby increasing the rate of formylation of 1,3,5-trialkyl-substituted aromatic compounds, 1,2,3,5-tetraalkyl-substituted aromatic compounds, 1,2,4,5-tetraalkyl-substituted aromatic compounds and 1,2,3,4,5-pentaalkyl-substituted aromatic compounds.

The amount of boron trifluoride used together with hydrogen fluoride as the catalyst is 1.0 to 2.5 mol, preferably 1.4 to 2.2 mol per one mole of the starting polyalkyl-substituted aromatic compound. If less than 1.0 mol, the formylation rate is unfavorably lowered because boron trifluoride is consumed in the formation of a firm complex with the polyalkyl-substituted aromatic aldehyde being produced. The use of boron trifluoride more than 2.5 mol is economically disadvantageous because no additional effect on improving the reaction rate is obtained and the amount of boron trifluoride to be recovered increases.

The formylation proceeds more rapidly as the carbon monoxide pressure increases. However, an excessively high pressure requires expensive apparatus. In the present invention, a carbon monoxide pressure of 1 to 3 MPa is sufficient. The formylation temperature is preferably –30 to 40° C.

The present invention will be described in more detail by reference to the following examples. However, it should be noted that the following examples are only illustrative and not intended to limit the scope of the invention thereto.

EXAMPLE 1

A 500-ml autoclave equipped with a stirrer, three upper inlet nozzles, one bottom outlet nozzle and a jacket for controlling the inner temperature was used as a formylation reactor.

Into the autoclave cooled to 0° C. or lower by flowing a cooling medium through the jacket, were charged 60 g (3.0 mol) of hydrogen fluoride and 120 g (1.0 mol) of mesitylene (MES). While controlling the temperature of the reaction solution to 20° C. or lower, 136 g (2.0 mol) of boron trifluoride was added under stirring.

After the addition of boron trifluoride, the inner pressure of the autoclave was increased to 2 MPa by introducing carbon monoxide while maintaining the inner temperature at 20° C. After stirring for one hour while maintaining the temperature at 20° C. and the pressure at 2 MPa, the whole reaction mixture was drawn from the reactor into ice water. The liquid mixture was added with heptane and mixed thoroughly by shaking, followed by separation of the oil layer, which was then washed with water and analyzed by gas chromatography. As shown in Table 1, the conversion of mesitylene was 57 mol % and the selectivity of mesityl aldehyde was 98 mol %.

EXAMPLE 2

The same procedure as in Example 1 was repeated except for changing the charge amount of hydrogen fluoride to 80 g (4.0 mol). The gas chromatographic analysis of the oil layer showed, as shown in Table 1, that the conversion of mesitylene was 48 mol % and the selectivity of mesityl aldehyde was 98 mol %.

EXAMPLE 3

The same procedure as in Example 1 was repeated except for changing the charge amount of hydrogen fluoride to 100 g (5.0 mol). The gas chromatographic analysis of the oil layer showed, as shown in Table 1, that the conversion of mesitylene was 41 mol % and the selectivity of mesityl aldehyde was 98 mol %.

EXAMPLE 4

The autoclave of the same type as used in Example 1 was cooled to –20° C., and then charged with 80 g (4.0 mol) of hydrogen fluoride and 120 g (1.0 mol) of pseudocumene. While controlling the liquid temperature to –20° C. or lower, 95 g (1.4 mol) of boron trifluoride was added under stirring.

After the addition of boron trifluoride, the inner pressure of the autoclave was increased to 2 MPa by introducing carbon monoxide while maintaining the inner temperature at –20° C. After stirring for 25 min while maintaining the temperature at –20° C. and the pressure at 2 MPa, the whole reaction mixture was drawn from the reactor into ice water. No trouble such as clogging of the outlet nozzle occurred. The liquid mixture was added with heptane and mixed thoroughly by shaking, followed by separation of the oil layer, which was then washed with water and analyzed by gas chromatography. The conversion of pseudocumene was 90 mol % and the selectivity of 2,4,5-trimethylbenzaldehyde was 99 mol %.

Comparative Example 1

The same procedure as in Example 1 was repeated except for changing the charge amount to 60 g (0.5 mol) for mesitylene, 100 g (5.0 mol) for hydrogen fluoride and 68 g (1.0 mol) for boron trifluoride. The gas chromatographic analysis of the oil phase showed that, as shown in Table 1, the conversion of mesitylene was 30 mol % and the selectivity of mesityl aldehyde was 98 mol %.

Comparative Example 2

The formylation was performed in the same manner as in Example 1 except for changing the charge amount of hydrogen fluoride to 40 g (2.0 mol). After the reaction, the reaction mixture was attempted to be drawn from the reactor. However, the outlet nozzle was clogged with red solids to fail to draw the whole reaction mixture. Therefore, after reducing the inner pressure, an additional portion of 40 g (2.0 mol) of hydrogen fluoride was added under stirring. The liquid drawn from the reactor was added with heptane and mixed thoroughly by shaking, followed by separation of the oil layer, which was then washed with water and analyzed by gas chromatography. As shown in Table 1, the conversion of mesitylene was 65 mol % and the selectivity of mesityl aldehyde was 98 mol %. The red solids that clogged the outlet nozzle disappeared when shaken with water after the addition of heptane. The analysis on the oil layer showed the presence of mesityl aldehyde and identified the solids as a mesityl aldehyde-HF-$BF_3$ complex.

TABLE 1

|  | Examples | | | Comparative Examples | |
| --- | --- | --- | --- | --- | --- |
|  | 1 | 2 | 3 | 1 | 2 |
| Starting materials (molar ratio) | | | | | |
| HF/MES | 3.0 | 4.0 | 5.0 | 10.0 | 2.0 |
| $BF_3$/MES | 2.0 | 2.0 | 2.0 | 2.0 | 2.0 |
| Reaction temperature (° C.) | 20 | 20 | 20 | 20 | 20 |
| Reaction pressure (MPa) | 2.0 | 2.0 | 2.0 | 2.0 | 2.0 |
| Conversion of MES (mol %) | 57 | 48 | 41 | 30 | 65 |
| Precipitation of solids | none | none | none | none | yes |

As seen from Examples and Comparative Example 1, the conversion of mesitylene that had alkyl groups on both the carbon atoms adjacent to the site to be formylated became higher as the amount of hydrogen fluoride used was reduced when compared in the same reaction time.

Also, as shown in Comparative Example 2, when the amount of hydrogen fluoride was smaller than the amount specified by the present invention, the conversion of the starting material increased, but the solid aldehyde-HF-$BF_3$ complex precipitated.

As seen from Examples and Comparative Examples, the rate of formylation of polyalkyl-substituted aromatic compounds that have alkyl groups on both the carbon atoms adjacent to the site to be formylated is increased by limiting the amount of hydrogen fluoride to the specific range. This enables the production of polyalkyl-substituted aromatic aldehydes under mild conditions without precipitation of solids.

What is claimed is:

1. A process for producing a polyalkyl-substituted aromatic aldehyde by a formylation of a polyalkyl-substituted aromatic compound having 3–5 $C_1$–$C_3$ alkyl groups with carbon monoxide in the presence of hydrogen fluoride and boron trifluoride, wherein the amount of hydrogen fluoride is 2.5 to 4.5 mol and the amount of boron trifluoride is 1.0 to 2.5 mol, each based on one mole of the polyalkyl-substituted aromatic compound.

2. The process according to claim 1, wherein the formylation is conducted at −30 to 40° C. under a pressure of 1 to 3 MPa.

3. The process according to claim 1, wherein the polyalkyl-substituted aromatic compound is at least one compound selected from the group consisting of 1,3,5-trialkyl-substituted aromatic compounds, 1,2,3,5-tetraalkyl-substituted aromatic compounds, 1,2,4,5-tetraalkyl-substituted aromatic compounds and 1,2,3,4,5-pentaalkyl-substituted aromatic compounds.

4. The process according to claim 1, wherein the polyalkyl-substituted aromatic compound is a 1,3,5-trialkyl-substituted aromatic compound.

5. The process according to claim 4, wherein the 1,3,5-trialkyl-substituted aromatic compound is mesitylene.

6. The process according to claim 1, wherein the amount of hydrogen fluoride is 3.0 to 4.5 mol based on one mole of the starting polyalkyl-substituted aromatic compound.

7. The process according to claim 6, wherein the amount of boron trifluoride is 1.4 to 2.2 mol per one mole of the starting polyalkyl-substituted aromatic compound.

8. The process according to claim 1, wherein the amount of boron trifluoride is 1.4 to 2.2 mol per one mole of the starting polyalkyl-substituted aromatic compound.

9. The process according to claim 1, wherein the polyalkyl-substituted aromatic compound is selected from the group consisting of isodurene, durene, pentamethylbenzene, 1-ethyl-3,5-dimethylbenzene, 1,3-diethyl-5-methylbenzene, 1-isopropyl-3,5-dimethylbenzene, 1,3,5-triisopropylbenzene and 1,2,3,5-tetraethylbenzene.

* * * * *